(12) United States Patent
Cichocki, Jr. et al.

(10) Patent No.: US 8,021,598 B2
(45) Date of Patent: *Sep. 20, 2011

(54) RAPID THERMAL TREATMENT FOR ENHANCING BENDING STIFFNESS AND YIELD MOMENT OF CURVED NEEDLES

(75) Inventors: Frank Richard Cichocki, Jr., Easton, PA (US); David Demarest, Parsippany, NJ (US); Gregory Hollin, Yardley, PA (US); Eugene D. Reynolds, Avon by the Sea, NJ (US)

(73) Assignee: Ethicon, Inc., Somerville, NJ (US)

( * ) Notice: Subject to any disclaimer, the term of this patent is extended or adjusted under 35 U.S.C. 154(b) by 679 days.

This patent is subject to a terminal disclaimer.

(21) Appl. No.: 11/956,105

(22) Filed: Dec. 13, 2007

(65) Prior Publication Data
US 2009/0157116 A1    Jun. 18, 2009

(51) Int. Cl.
*C21D 9/26*    (2006.01)
*C21D 9/56*    (2006.01)
*C21D 9/00*    (2006.01)

(52) U.S. Cl. ........ 266/105; 266/102; 266/103; 266/249; 266/252; 148/559; 148/572

(58) Field of Classification Search .................. 266/102, 266/103, 105, 249, 252; 148/559, 572
See application file for complete search history.

(56) References Cited

U.S. PATENT DOCUMENTS

| | | | |
|---|---|---|---|
| 4,295,033 A * | 10/1981 | Lindgren et al. | 219/388 |
| 4,501,312 A | 2/1985 | Matsutani | |
| 5,415,707 A | 5/1995 | Bendel et al. | |
| 5,630,268 A | 5/1997 | Smith et al. | |
| 5,935,411 A * | 8/1999 | Brown et al. | 205/672 |
| 5,968,394 A | 10/1999 | Schob | |
| 7,001,472 B2 | 2/2006 | Collier et al. | |
| 2008/0147117 A1 * | 6/2008 | Cichocki et al. | 606/223 |
| 2008/0147118 A1 | 6/2008 | Cichocki | |
| 2008/0295927 A1 | 12/2008 | Cichocki et al. | |

FOREIGN PATENT DOCUMENTS

| | | |
|---|---|---|
| EP | 0646352 | 4/1995 |
| JP | 55058324 | 5/1980 |
| JP | 2002143172 | 5/2002 |

* cited by examiner

*Primary Examiner* — Roy King
*Assistant Examiner* — Lois Zheng
(74) *Attorney, Agent, or Firm* — Roberts Mlotkowski Safran & Cole, P.C.

(57) ABSTRACT

An apparatus for thermally treating a plurality of curved suture needles. The apparatus includes a conveyer for transferring the plurality of curved suture needles from a source of curved suture needles to a receiver, a housing positioned adjacent the conveyer, the housing having a first end, a second end, and an opening running from the first end to the second end, the opening aligned with the conveyer to enable the plurality of curved suture needles to pass therethrough, and a heat source located within the housing for heating the plurality of curved suture needles as the plurality of curved suture needles are transferred by the conveyer from the first end of the housing to the second end of the housing. Also provided is a process for thermally treating a plurality of curved suture needles to enhance the stiffness and yield moment of the curved suture needles. The curved suture needles so treated have a desirable combination of stiffness, strength and ductility.

9 Claims, 6 Drawing Sheets

RAPID THERMAL TREATMENT FOR ENHANCING BENDING STIFFNESS AND YIELD MOMENT OF CURVED NEEDLES

FIELD OF THE INVENTION

The present invention relates to an apparatus and process for producing suture needles having a desirable combination of stiffness, strength and ductility. More specifically, the present invention relates to an apparatus and process for producing suture needles that exhibit superior bending stiffness properties.

BACKGROUND OF THE INVENTION

Certain surgeries, particularly coronary artery bypass surgery, necessarily involve the use of suture needles of small diameter having exceedingly high bending stiffness and strength. In particular, surgeries of this type require that the suture needle's path be closely controlled. In the event that a needle were to flex excessively as it entered the tissue or as it pierced the inner surface of a blood vessel before re-emerging, improper placement of the needle and serious trauma to the tissue and the patient could possibly occur.

In use, suture needles are subjected to forces sufficient to overcome frictional drag through the tissue. These forces, which tend to resist needle penetration, may be greater in patients undergoing cardiovascular surgery who exhibit calcified or toughened tissue due to coronary artery disease. In these procedures, the suture needle must be able to pass through not only the blood vessel, but also any hard calcified tissue that may be located along the periphery of the blood vessel lumen. An overly compliant needle may deflect elastically during tissue penetration and may result in some loss of placement control. As such, it is preferable that the needle should have a relatively high bending stiffness, that is, a low tendency to flex and high tendency to retain its configuration when subjected to a deforming force. Hence, stiffness in bending is a desirable property for the handling and performance of suture needles. A stiff needle resists elastic deflection and can thus be directed as intended to provide a high level of control.

ASTM Standard F1840-98a (Reapproved 2004) provides standard terminology for surgical suture needles and ASTM standard F1874-98 (Reapproved 2004) provides details of a standard test method for bend testing of needles used in surgical sutures. Both ASTM standards are incorporated herein by reference in their entirety. Two different measures for the strength of surgical suture needles are used, namely, yield bend moment, which is the amount of moment required to initiate plastic deformation during a bend test, and maximum bend moment, which is the greatest moment applied to a needle during a bend test. This later value of maximum bend moment is typically measured at a point where the needle has undergone substantial plastic deformation and is generally higher than the yield bend moment or point at which plastic deformation initiates. The point of deflection at which plastic deformation initiates, or more formally according to ASTM standards, the angle at which the yield bend moment occurs, is referred to as the yield bend angle.

The vast majority of suture needles used in the practice of medicine are curved. The curvature of the needle enables exact placement and guidance through the surrounding tissue. Curvatures may be slight, for example equivalent to a one-quarter circle, or may be pronounced for example equal to or in excess of one-half circle. Suture needles are conventionally produced by curving straight wire to the desired degree. However, in the process of mechanically curving the suture needle, residual stresses are produced that may serve to weaken the needle and may make it susceptible to bending or opening against the curvature when stress is imparted in the course of surgery. Indeed, the yield moment required to bend a curved suture needle may be substantially less than the yield moment required to bend a straight needle. Thermal processes for relieving the residual stresses imparted during the needle curving process have been developed to improve strength and stiffness of the suture needle.

Both needle bending strength and needle bending stiffness influence handling characteristics, as well as penetration performance and efficacy of the suture needle. It is important to note that in almost all circumstances, the suture needle should be used in applications where the yield bend moment is not exceeded, since above this value, the needle may bend plastically, may lose its original shape, and may no longer function as intended. It is thus apparent that a desirable characteristic of a suture needle is a high yield bend moment, which is a manifestation of the bending strength of the suture needle. Below the yield bend moment, the resistance to bending of the suture needle is best characterized by the needle bending stiffness.

Needle bending stiffness is a critical measure of the resistance to elastic or recoverable bending of the suture needle before needle deflection reaches the yield bend angle and can be calculated as the yield bend moment divided by the yield bend angle. If a straight or curved suture needle has a low value of bending stiffness, substantial bending of the needle may occur for a given bend moment, whereas if a straight or curved suture needle exhibits a high bending stiffness value, relatively little elastic bending of the needle will occur for a given bend moment. Surgeons tend to perceive a high degree of elastic bending as a loss of control or as poor penetration performance since the needle point is not translating directly with the motion of their hands. As such, needle bending stiffness may be recognized as an important measure of needle performance in most surgical applications.

Hence, desirable bend properties for a suture needle are high bending stiffness, as well as bending strength manifested as high yield bend moment and ductility, in order to penetrate tissue which is being sutured without undue flexing, plastic bending, or breaking during a surgical procedure.

The needle should also not be brittle; if any portion of the needle is too brittle it may break during use if too much force is applied. The needle should instead be ductile, which is the ability to bend without breaking. Curved suture needles are commonly bent through a bend angle of 90 degrees and then manually reshaped to their original curvature to assess ductility. Those skilled in the art of needle making will recognize this procedure as the reshaping process and will further recognize that the higher the number of reshape processes that a needle can withstand without breaking the more ductile it is.

Processes for the thermal treatment of suture needles for the purpose of improving yield moment and stiffness have largely been ignored. This is especially true for stainless steel suture needle materials that do not undergo martensitic transformations such as the 302 SS, 304 SS, 316 SS, 4310 SS, and the like, which employ work hardening, imparted during wire drawing and needle forming operations, as their primary strengthening mechanisms. By way of exception, martensitic and martensitic-aged stainless steels such as 420 SS, 455 SS, 465 SS and others are conventionally subjected to batch heat treatment to drive either a martensitic transformation for strength, precipitation of a strengthening phase, and/or tempering of the alloy to enhance ductility. However, these processes have not been designed expressly for enhanced stiffness and yield moment.

In view thereof, there remains a long-felt need for an apparatus and process for rapidly thermally treating a suture needles for enhanced stiffness and yield moment.

SUMMARY OF THE INVENTION

In one aspect, provided is an apparatus for thermally treating a plurality of curved suture needles. The apparatus includes a conveyer for transferring the plurality of curved suture needles from a source of curved suture needles to a receiver, a housing positioned adjacent the conveyer, the housing having a first end, a second end, and an opening running from the first end to the second end, the opening aligned with the conveyer to enable the plurality of curved suture needles to pass therethrough, and a heat source located within the housing for heating the plurality of curved suture needles as the plurality of curved suture needles are transferred by the conveyer from the first end of the housing to the second end of the housing.

In another aspect, provided is a process for thermally treating a plurality of curved suture needles to enhance the stiffness and yield moment of the curved suture needles. The process includes the steps of conveying the plurality of curved suture needles from a source of curved suture needles to a receiver, heating the plurality of curved suture needles to a temperature below the recrystallization temperature of the curved suture needles as the plurality of curved suture needles pass between the source of curved suture needles and the receiver, and providing a shielding gas to minimize oxidation and degradation of the plurality of curved suture needles as the plurality of suture needles are heated.

In one embodiment, a system for providing a shielding gas is utilized to minimize oxidation and degradation of the plurality of curved suture needles as the plurality of suture needles pass through the housing. The system for providing a shielding gas may also substantially prevent excessive heat transfer to the conveyer.

In another embodiment, the shielding gas is hydrogen, argon, nitrogen, neon, helium, CO, $CO_2$ or mixtures thereof.

In yet another embodiment, the conveyer includes a strip or plurality of strips to which the plurality of curved suture needles are attached.

The apparatus and processes provided herein enable the continuous and rapid passage of curved suture needles through a concentrated heat source to relieve residual stresses or impart a microstructural change to enhance strength and stiffness. The processes offer savings in time and expense over more conventional batch heat treatments and are compatible with a wide variety of needle carrier strip materials conventionally used to transport and prevent damage to the suture needles. With the use of shielding gas, even paper tape carrier strips may be used to convey suture needle past a heat source having a temperature in excess of 1500° C.

These and other advantages, features and attributes of the disclosed apparatus and processes and their advantageous applications and/or uses will be apparent from the detailed description that follows, particularly when read in conjunction with the figures appended hereto.

DETAILED DESCRIPTION OF THE INVENTION

Definitions

Unless defined otherwise, all technical and scientific terms used herein are intended to have the same meaning as is commonly understood by one of ordinary skill in the relevant art.

As used herein, the singular forms "a," "an," and "the" include the plural reference unless the context clearly dictates otherwise.

As used herein, "bending stiffness" (stiffness in bending) means the resistance to elastic deformation of a curved suture needle.

As used herein, "diameter" herein is meant the square root of $(4A/\pi)$, wherein A is the cross-sectional area.

As used herein, "ductile-to-brittle-transition-temperature" (DBTT) means the temperature above which a substantial improvement in ductility of an alloy occurs. When used herein, the DBTT is determined as the temperature at which the alloy exhibits at least 5% elongation to break in a tensile test.

As used herein, "ductility" is the ability of an alloy to withstand plastic deformation without breaking.

As used herein, "elastic deformation" is the deformation, strain, or displacement that is recoverable by removing the applied load.

As used herein, "elongation-to-break" is a measurement of sample percent elongation in a simple tension test used to assess alloy ductility.

As used herein, an "I-beam needle body" refers to any variety of needle body designs that incorporate flattened opposed sides, instead of an entirely round design.

As used herein, "material properties" means the properties of the material only, derived by testing in a manner in which needle shape and surface properties do not influence data. Examples include: Young's modulus, ultimate tensile strength (when tested in simple tension), and microhardness hardness.

As used herein, a "needle blank" is an elongate piece of wire, a portion of which is converted via multiple processes into the shape of a suture needle. Also, as used herein, "needle blank" refers to a portion of wire extending from the proximal end of the suture needle used to move and position the suture needle for processing in accordance herewith.

As used herein, "recrystallization temperature" is the temperature at which new grains will form in the microstructure of an alloy.

As used herein, "simple tension" is the tension applied in one dimension, with other dimensions being unconstrained.

As used herein, "thermal forming" means the plastic forming conducted on a heated work piece.

As used herein, "ultimate bending moment" means the greatest moment applied to a needle during bend testing conducted under ASTM Standard F-1840-98a.

As used herein, "yield bending moment" means the amount of moment required to initiate plastic deformation during bend tests conducted under ASTM standard F-1840-98a.

Reference is now made to FIGS. 1-8B, wherein like numerals are used to designate like parts throughout.

Referring now to FIGS. 1-4, an apparatus 10 for thermally treating a plurality of curved suture needles is shown. The apparatus includes a conveyer 12 for transferring the plurality of curved suture needles 14 from a source of curved suture needles 16 to a receiver 18. Conveyer 12 may be formed from a strip comprised at least in part of metal, paper, or plastic, wherein mechanical attachment may be achieved by bending a preformed tab (not shown) connected to a metal strip around at least a portion of each of the plurality of curved suture needles 14 or, alternatively, a pressure sensitive adhesive may be coated on at least one surface of the paper, plastic, or metal carrier strip, or, alternatively, at least one weld is utilized to affix each of the plurality of curved suture needles 14 to the metal carrier strip.

Figure 1:
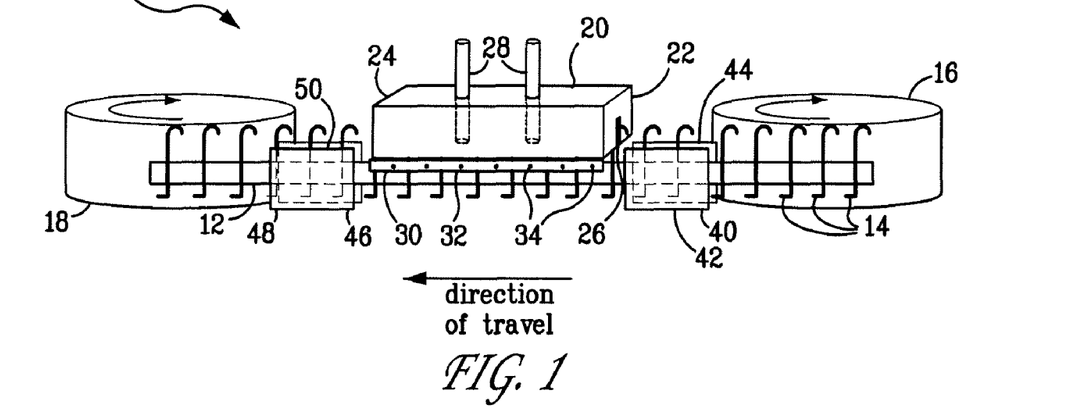
FIG. 1 is a schematic representation of an apparatus for thermally treating a plurality of curved suture needles, in accordance herewith.

Apparatus 10 also includes a housing 20 positioned adjacent conveyer 12. Housing 20 includes a first end 22, a second end 24 and an opening 26 extending from first end 22 to second end 24. As shown, opening 26 is aligned with conveyer 12 to enable the plurality of curved suture needles 14 to pass through housing 20.

Housing 20 also includes a heat source 28 located within housing 20 for heating the plurality of curved suture needles 14 as the plurality of curved suture needles 14 are transferred by conveyer 12 from the first end 22 of housing 20 to the second end 24 of housing 20. Heat source 28 may be a conventional heat source and may include one or more electrical resistance heating elements, one or more inductively coupled heating elements, a hot gas stream, or the like. By employing a narrow opening 26 for needle 14 passage, excessive radiative heat transfer to the conveyer 12 is minimized or prevented. To further enhance the ability of housing 20 to minimize or prevent excessive radiative heat transfer to conveyer 12, housing 20 may also employ insulative material (not shown) within its interior and/or on its exterior surfaces.

Figure 2:
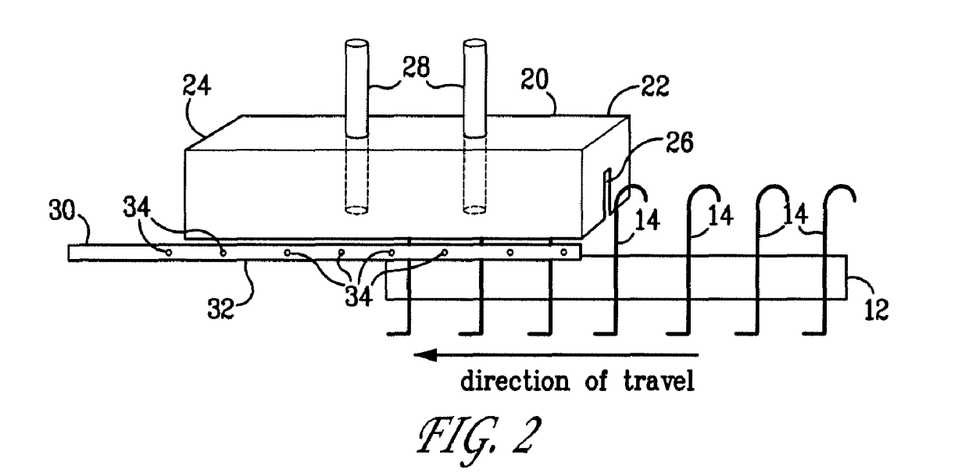
FIG. 2 is a schematic representation of a heat source for use in an apparatus for thermally treating a plurality of curved suture needles, in accordance herewith.
Figure 4:
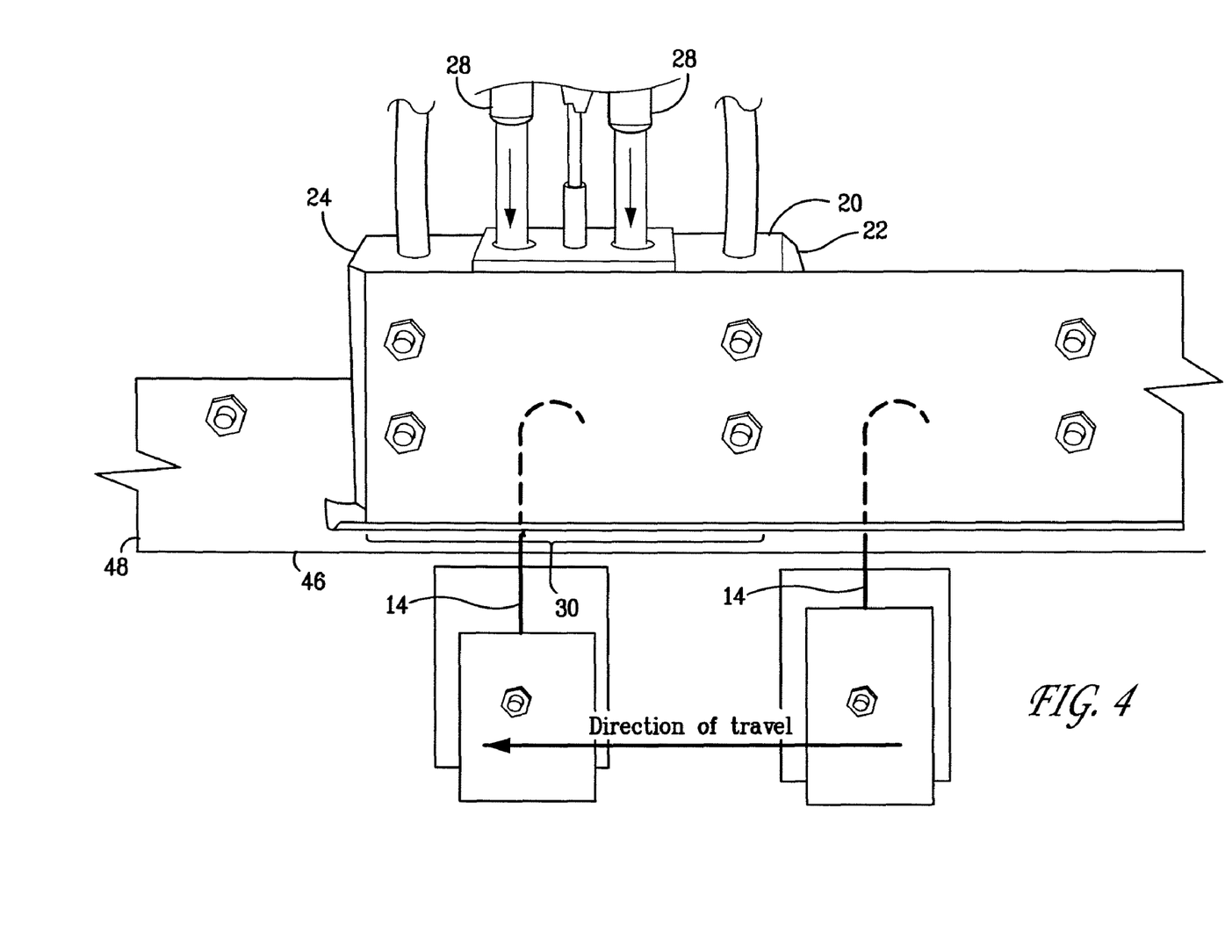
FIG. 4 shows one embodiment of an apparatus for thermally treating a plurality of curved suture needles, focusing on a heat source and guide, in accordance herewith.

As shown in FIGS. 1, 2 and 4, apparatus 10 may further include a system for providing a shielding gas 30 to minimize oxidation and degradation of the plurality of curved suture needles 14 as the plurality of suture needles 14 pass through housing 20. The system for providing a shielding gas 30 may include a gas supply wand 32 having a plurality of ports 34 for emitting the shielding gas. The shielding gas employed herein may be hydrogen, argon, nitrogen, neon, helium, CO, $CO_2$ or mixtures thereof. System for providing a shielding gas 30 may advantageously substantially prevent excessive heat transfer to the conveyer 12.

As shown in FIGS. 1 and 4, apparatus 10 may also include a guide for positioning the plurality of curved suture needles 40 to substantially center the plurality of curved suture needles 14 within opening 26 of housing 20. In one embodiment, apparatus 10 includes a first guide 40 for positioning the plurality of curved suture needles 14 to substantially center the plurality of curved suture needles 14 within opening 26 of housing 20. As shown, first guide 40 for positioning the plurality of curved suture needles 14 is located between housing 20 and the source of curved suture needles 16. In one embodiment, first guide 40 for positioning the plurality of curved suture needles 14 may include a first plate 42 and a second plate 44, positioned in a spaced parallel relationship. In another embodiment, apparatus 10 may also include a second guide 46 for positioning the plurality of curved suture needles 14 to substantially center the plurality of curved suture needles 14 as they exit opening 26 of housing 20. As shown, second guide 46 for positioning the plurality of curved suture needles 14 is located between housing 20 and the receiver 18. Second guide 46 for positioning the plurality of curved suture needles 14 may include a first plate 48 and a second plate 50, positioned in a spaced parallel relationship.

Figure 3:
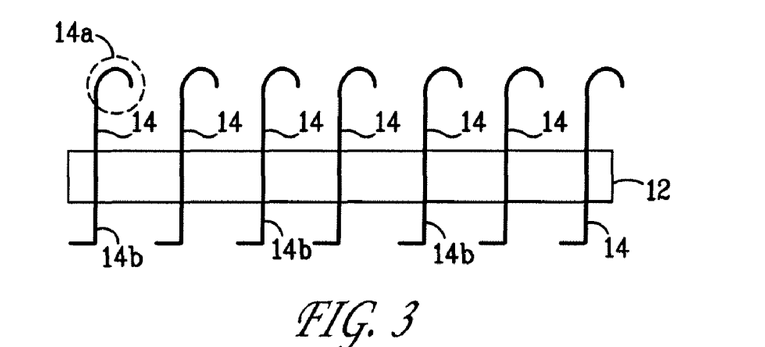
FIG. 3 is a schematic representation of a plurality of curved suture needles attached to a carrier strip, in accordance herewith.

As shown in FIG. 1, in one embodiment, the source of curved suture needles 16 includes a pay-off spool. In another embodiment, receiver 18 includes a take-up spool. As shown in FIG. 3, each of the plurality of curved suture needles 14 may include a curved suture needle portion 14a and a needle blank 14b. Needle blank 14b has utility in that it may be affixed to conveyer 12, as described hereinabove.

In another embodiment, provided is a process for thermally treating a plurality of curved suture needles 14 to enhance the stiffness and yield moment of the curved suture needles 14. The process comprising includes steps of conveying the plurality of curved suture needles 14 from a source of curved suture needles 16 to a receiver 18, heating the plurality of curved suture needles 14 to a temperature below the recrystallization temperature of the curved suture needles 14 as the plurality of curved suture needles 14 pass between the source of curved suture needles 16 to the receiver 18, and providing a shielding gas to minimize oxidation and degradation of the plurality of curved suture needles 14, as the plurality of suture needles 14 are heated.

In one embodiment, the plurality of curved suture needles 14 is heated to a temperature ranging from about 350 to about 1900° C. for about 1 second to about 5 minutes, or from about 400 to about 1650° C. for about 2 second to about 5 minutes.

As will be described in more detail below, in one embodiment, the plurality of curved suture needles 14 includes a tungsten alloy. In another embodiment, the plurality of curved suture needles 14 includes at least one or more metals selected from the group consisting of rhenium, tantalum or molybdenum. In yet another embodiment, the plurality of curved suture needles 14 includes up to 30 weight percent rhenium and the balance tungsten.

In one embodiment, the plurality of curved suture needles 14 is heated in an inert or reducing atmosphere. In another embodiment, the plurality of curved suture needles 14 is heated in an oxidizing atmosphere.

In one embodiment, the process disclosed herein is a rapid continuous process wherein the mechanism for stiffness and yield moment enhancement is selected from one of the following: 1) stress relief, 2) martensitic transformation and stress relief, 3) precipitation strengthening and stress relief and 4) tempering and stress relief. In one embodiment, the curved suture needles 14 are comprised of a tungsten alloy, a steel alloy, or a molybdenum alloy.

The mechanism of stress relief, alone, may be applied to tungsten alloys, molybdenum alloys, and certain austenitic steel alloys such as 302 SS, 304 SS, 316 SS, 4310 SS and the like. The mechanism of matensitic transformation plus stress relief may be applied to certain martensitic steels such as alloy 420 SS. Precipitation strengthening plus stress relief may be applied to martensitic-aged stainless steels such as 455 SS, 465 SS. Tempering plus stress relief may be applied to martensitic and some martensitic-aged steels, with particular application to 420 SS.

It is important to note that, certain stainless steels are prone to embrittlement via the formation of chrome carbides or sigma phase when heat treated for durations of several minutes or more in the temperature range of about 400 to about 1000° C. This may be particularly true of the austenitic stainless steels listed above. The continuous heat treatments described herein may prevent the formation of these embrittling phases by rapidly processing at higher temperatures where these embrittling phases are not thermodynamically prone to formation, or by not allowing sufficient time for formation or growth of these embrittling phases.

As indicated above, the suture needles may be formed from an alloy of tungsten. The tungsten alloy may comprise one or more metals selected from the group consisting of rhenium, osmium, tantalum, or molybdenum. In one embodiment, the alloy may be a tungsten-rhenium alloy, and has no more than trace amounts of other elements present. The metal other than tungsten may be present in an amount up to about 30 weight percent of the alloy, or in an amount ranging from about 20 to about 26 weight percent of the alloy.

The suture needle may have a diameter effective to permit satisfactory usage in fine surgery. Typically, the diameter will be less than about 60 mils (thousandths of an inch), or less than about 15 mils, down to about 1 mil, or about 1.4 to about 12 mils. It will be recognized that the suture needle may have a circular body cross-section, and that the needle may also be of a non-circular cross-sectional shape such as triangular; trapezoidal; rectangular; hexagonal; elliptical; or rectangular wherein the opposed shorter ends of the rectangle are rounded into semicircles. The needle may be provided with a "ribbon" shape with a single set of opposing flat sides, or a rectangular or "I-beam" shape, or with a cross-section which smoothly undergoes transition from the point to a circular cross-section, to a rectangular cross-section having rounded and then sharper corners, as described in U.S. Pat. No. 4,799,484, the contents of which are herein incorporated by reference in their entirety.

The suture needle may be straight or curved, but the improvement in bending strength and stiffness disclosed and achieved herein is especially advantageous for curved needles. In one embodiment, the needle is curved through a radius of curvature, which need not be constant but is preferably constant. Thus, shapes of the needles disclosed herein include sections of a circle, such as a quarter circle, three-eighths circle, half circle, or five-eighths of a circle.

Following the final drawing of the tungsten alloy or stainless steel wire to the final desired diameter, one end of the needle is given a point having the desired shape, the point being provided by any conventional technique such as grinding. Optionally, the body may be formed by pressing or grinding operations into the variety of shapes. The needle may then be given its desired curvature, typically by rolling around a mandrel of the desired radius of curvature. The opposite end of the needle is given an opening in its end, or other means by which the end of a suture can be attached to the needle by swaging or the like.

In order to impart improved bending strength and stiffness to the suture needle described herein, particularly after a curvature has been imparted to the needle, the curved needle is heated to a temperature below the recrystallization temperature of the tungsten alloy. In one embodiment, the suture needle is heated to a temperature ranging from about 350 to about 1900° C. In another embodiment, the suture needle is heated to a temperature ranging from about 400 to about 1650° C. in an inert or reducing atmosphere for about 1 second to about 5 minutes to impart bending stiffness to the surgical needle.

Advantageously, as described above, the curved suture needles 14 are attached to a conveyer material and passed in the vicinity of a heat source 28. In this way, the exposure time to elevated temperature is limited, since higher temperatures for shorter periods of time are effective to achieve the desired stiffening effect.

In another embodiment, the curved suture needles 14 are heated to a temperature ranging from about 350 to about 900° C. in an oxidizing atmosphere, in order to impart a robust adherent black, blue, or yellow oxide surface coating to the tungsten alloy suture needle described herein. Exposure time may range from seconds to several minutes, depending upon the temperature or temperatures may range from about 400 and about 800° C. for duration of about 1 second to about 5 minutes. Examples of an oxidizing atmosphere include, but are not limited to, oxygen-rich atmosphere, air, or a carbon dioxide/carbon monoxide gas mixture that decomposes or reacts with the tungsten alloy surface to form an oxide.

In another embodiment, the curved suture needles 14 may first be heated to a temperature ranging from about 350 to about 1900° C. in an inert or reducing atmosphere, followed by heating to a temperature ranging from about 350 to about 900° C. in an oxidizing atmosphere, to impart improved bending stiffness and a robust adherent black, blue, or yellow surface coating to the tungsten alloy suture needles.

The curved suture needles 14 produced as described herein may also be provided with a coating, for instance, a polymeric coating, in accordance with known techniques, if desired. The needle is then attached to the suture, packaged and sterilized, again in accordance with conventional techniques.

The curved suture needles 14 produced as described herein are characterized by a desirable combination of bending stiffness, strength and ductility. For the curved suture needles 14 produced as described herein, the wire tensile yield strength is generally at least about 250,000 ksi. High wire tensile yield strength is useful as it indicates the ability of the needles to withstand potentially deforming stresses without suffering permanent deformation.

The wire from which the curved suture needles 14 are made also exhibits uniquely high Young's modulus of elasticity, generally at least about 400 GPa. The high Young's modulus is desirable in that it reflects the potential for higher stiffness and the ability of the curved suture needles 14 produced as described herein to withstand potentially deforming stresses by retaining their shape, without undue flexing. However, in practice, as described above, a high Young's modulus of the wire alone does not directly translate into a high bending stiffness for a curved suture needle 14. Indeed to capitalize on the intrinsic material stiffness, a heat treatment is applied to the curved suture needles 14, as described hereinabove.

The following examples are provided for purposes of illustration and should not be interpreted as limiting in any way the scope of the claims appended hereto.

EXAMPLES

Example 1

Figure 5:
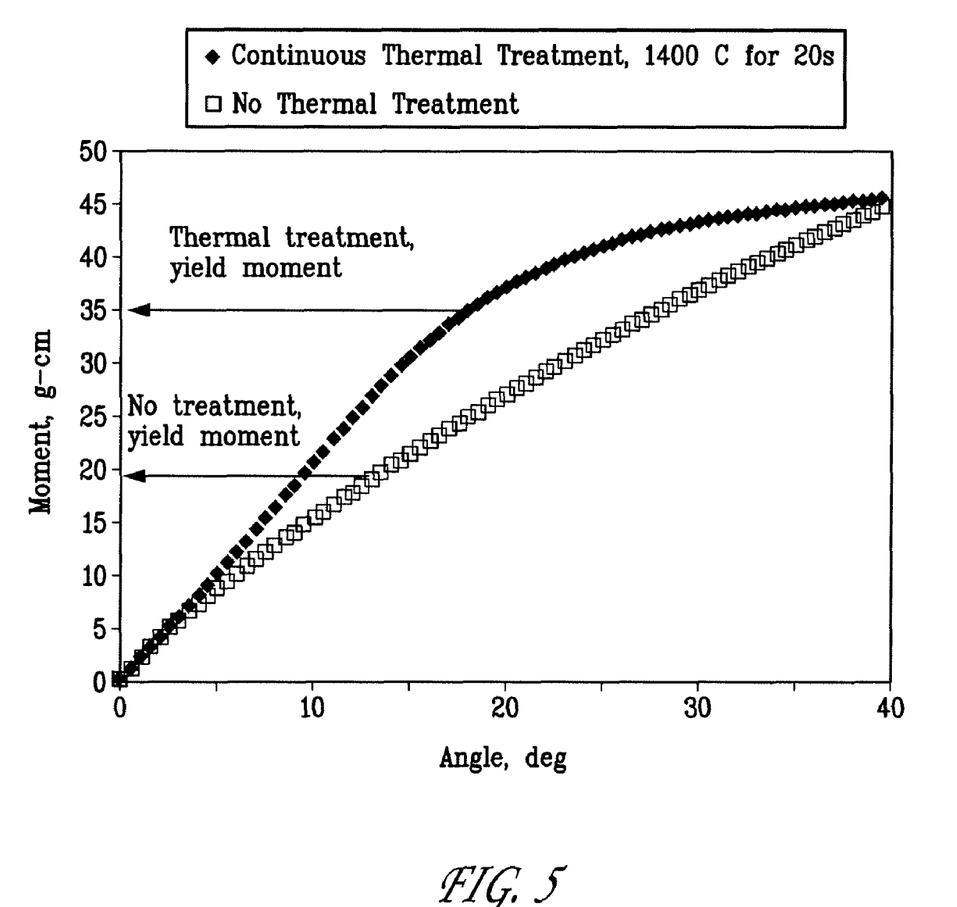
FIG. 5 is a graph comparing the bending performance of a 0.008" diameter curved suture needle produced from a tungsten 26% rhenium alloy that has been subjected to a continuous rapid thermal treatment at 1400° C. for 20 seconds compared to an equivalent tungsten 26% rhenium alloy suture needle that has received no thermal treatment.

A graph comparing the bending performance of a heat treated curved 0.008" diameter suture needle produced from a tungsten 26% rhenium alloy that has been subjected to a continuous rapid thermal treatment at 1400° C. for 20 seconds is compared to an equivalent tungsten 26% rhenium alloy suture needle that has received no thermal treatment is provided in FIG. 5.

All tests were conducted according to ASTM standard F1874-98. The yield bend moment and yield bend angle are marked on the graph. The slope of the tungsten-rhenium alloy suture needle up to the yield bend moment represents bending stiffness and is markedly greater than that provided by the equivalent untreated tungsten 26% rhenium alloy. The heat treatment applied to the tungsten alloy suture needle was conducted under an argon 2% hydrogen atmosphere at 1400° C. for 20 seconds.

Example 2

Figure 6:
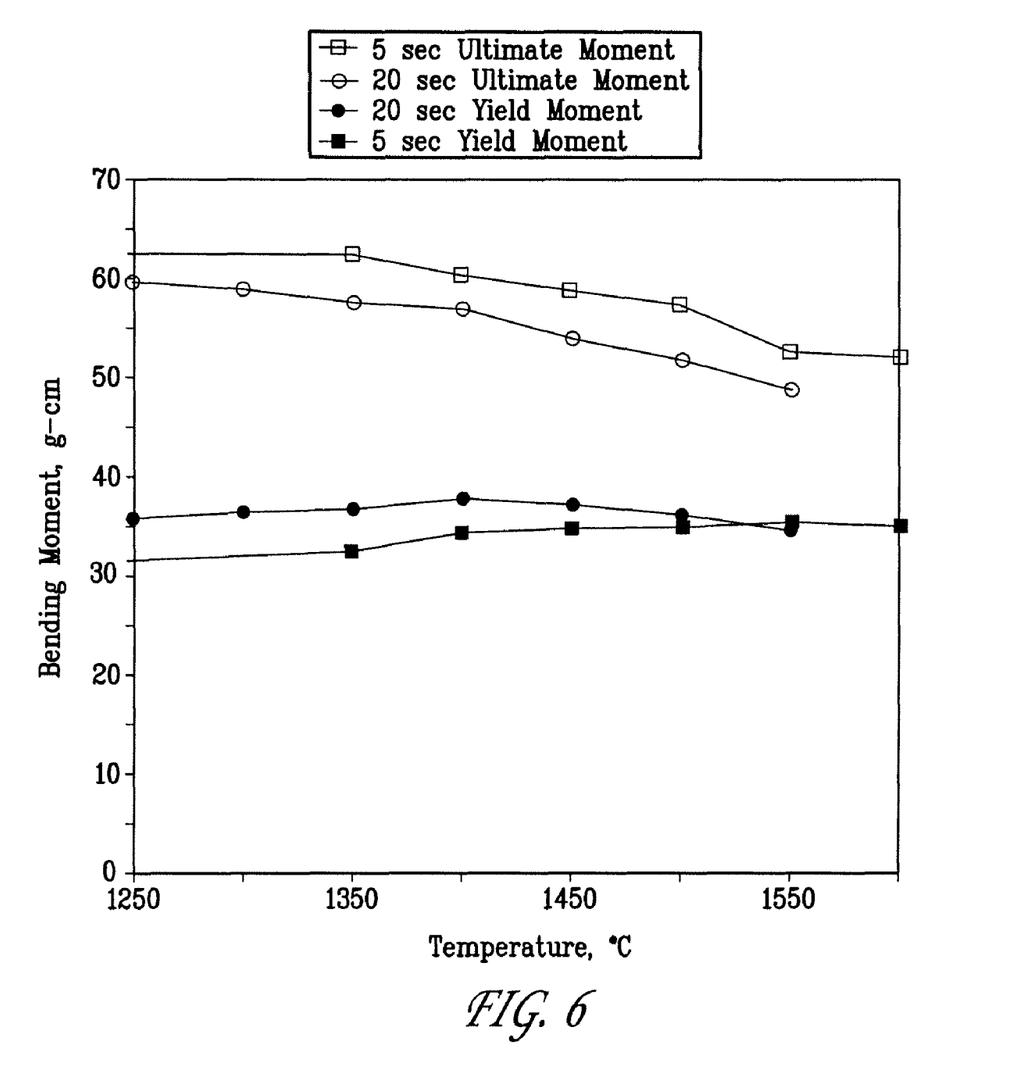
FIG. 6 is a graph showing the effect of temperature and time on yield moments and ultimate moments of a 0.008" diameter curved suture needles produced from a tungsten 26% rhenium alloy.

A graph showing the effect of temperature and time on yield moments and ultimate moments of a 0.008" diameter curved suture needle produced from a tungsten 26% rhenium alloy is presented in FIG. 6. Rapid thermal treatment was conducted at durations of 5 and 20 seconds over a broad temperature range under argon 2% hydrogen gas to maintain an inert non-oxidizing atmosphere. Yield moments in excess of 30 g-cm were achieved. All tests were conducted according to ASTM standard F1874-98.

Example 3

Figure 7A:
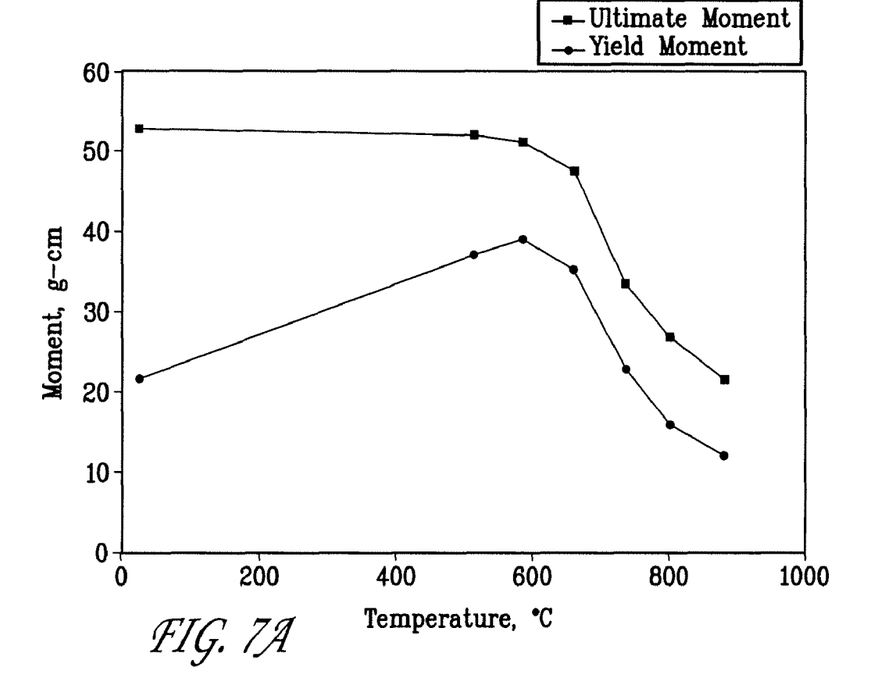
FIG. 7A shows the influence of temperature applied over 20 seconds on the yield moment and ultimate moment of 0.008" diameter curved suture needles produced from austenitic alloy stainless steel series 4310.
Figure 7B:
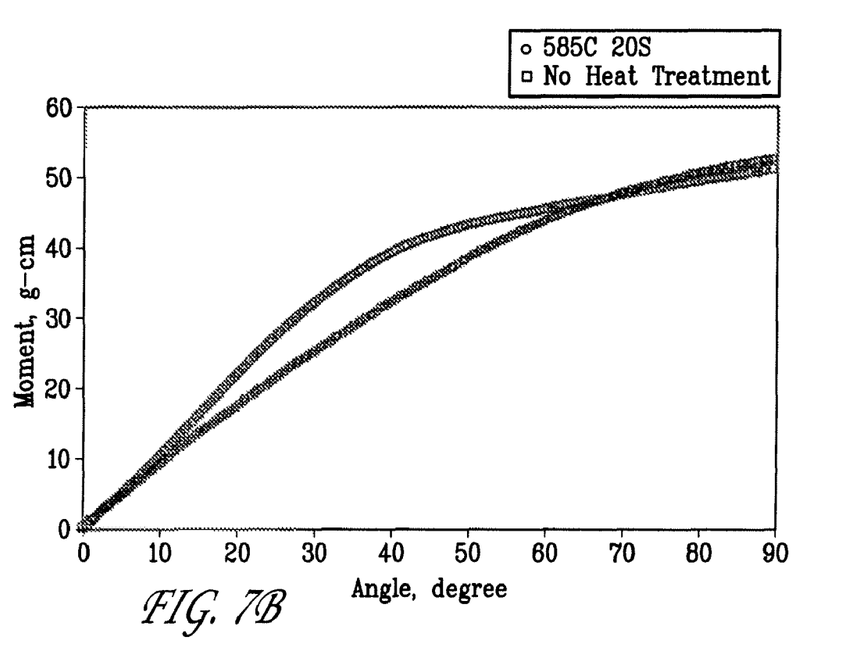
FIG. 7B shows a comparison of bending performance for a stainless steel series 4310 alloy needle, with and without rapid heat treatment.

FIG. 7A shows the influence of temperature applied over 20 seconds on the yield moment and ultimate moment of 0.008" diameter curved suture needles produced from austenitic alloy stainless steel series 4310. FIG. 7B shows a comparison of bending performance for a stainless steel series 4310 alloy needle, with and without rapid heat treatment in accordance herewith. All tests were conducted in substantial accordance with ASTM standard F1874-98.

Example 4

Figure 8A:
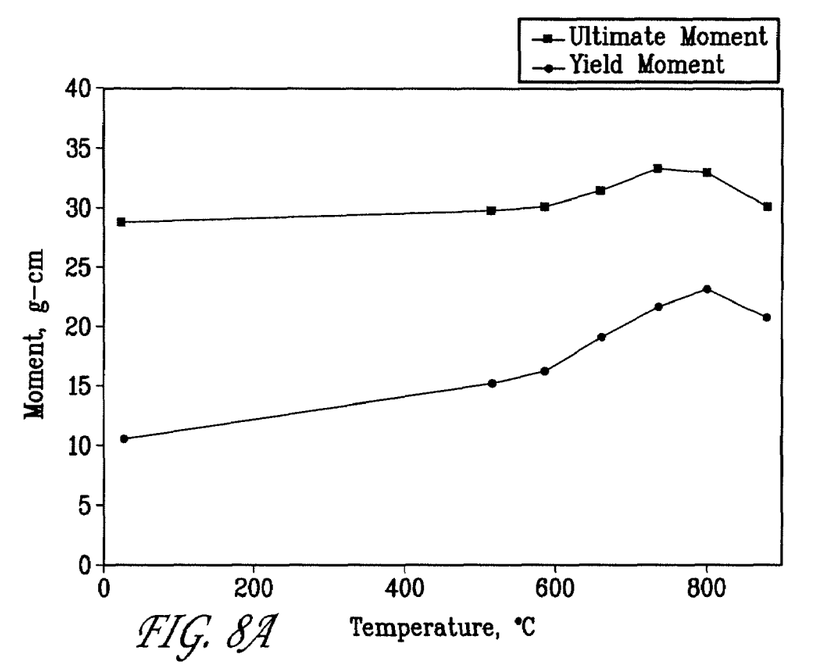
FIG. 8A shows the influence of temperature applied over 20 seconds on the yield moment and ultimate moment of 0.008" diameter curved suture needles produced from a martensitic-aged stainless steel.
Figure 8B:
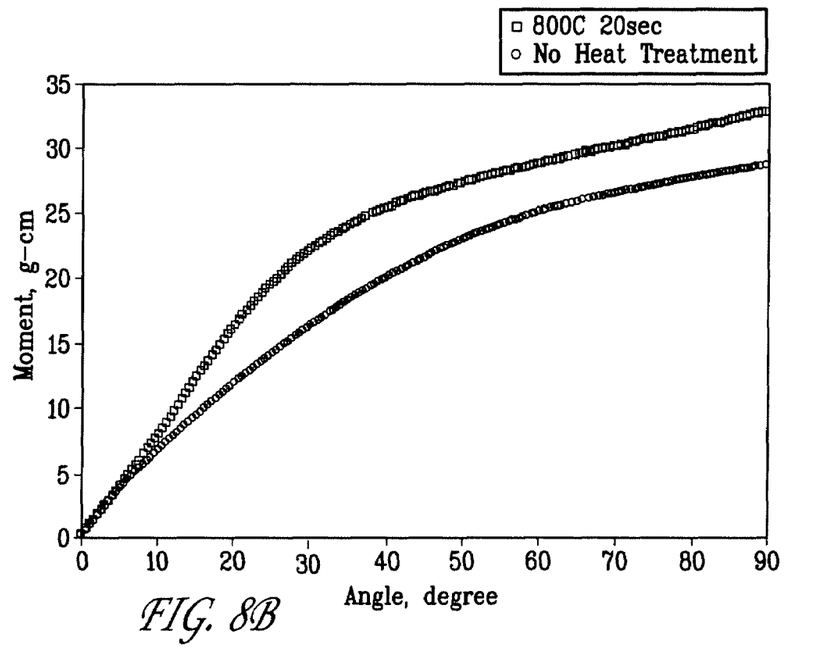
FIG. 8B shows a comparison of bending performance for a martensitic-aged stainless steel needle, with and without rapid heat treatment.

FIG. 8A shows the influence of temperature applied over 20 seconds on the yield moment and ultimate moment of 0.008" diameter curved suture needles produced from a martensitic-aged stainless steel. FIG. 8B shows a comparison of bending performance for a martensitic-aged stainless steel needle, with and without rapid heat treatment. All tests were conducted in substantial accordance with ASTM standard F1874-98.

All patents, test procedures, and other documents cited herein, including priority documents, are fully incorporated by reference to the extent such disclosure is not inconsistent and for all jurisdictions in which such incorporation is permitted.

While the illustrative embodiments disclosed herein have been described with particularity, it will be understood that various other modifications will be apparent to and can be readily made by those skilled in the art without departing from the spirit and scope of the disclosure. Accordingly, it is not intended that the scope of the claims appended hereto be limited to the examples and descriptions set forth herein but rather that the claims be construed as encompassing all the features of patentable novelty which reside herein, including all features which would be treated as equivalents thereof by those skilled in the art to which this disclosure pertains.

When numerical lower limits and numerical upper limits are listed herein, ranges from any lower limit to any upper limit are contemplated.

What is claimed is:

1. An apparatus for thermally treating a plurality of curved suture needles, the apparatus comprising:
   a) a conveyer for transferring the plurality of curved suture needles from a source of curved suture needles to a receiver;
   b) a housing positioned adjacent said conveyer, said housing having a first end, a second end, and an opening running from said first end to said second end, said opening aligned with said conveyer to enable the plurality of curved suture needles to pass therethrough;
   c) a heat source located within said housing for heating the plurality of curved suture needles as the plurality of curved suture needles are transferred by said conveyer from said first end of said housing to said second end of said housing;
   d) a first guide for positioning the plurality of curved suture needles to substantially center the plurality of curved suture needles within the opening of said housing said first guide for positioning the plurality of curved suture needles located between said housing and said source of curved suture needles; and
   e) a second guide for positioning the plurality of curved suture needles to substantially center the plurality of curved suture needles within the opening of said housing, said second guide for positioning the plurality of curved suture needles located between said housing and said receiver
   wherein said first guide includes a first plate and a second plate, positioned in a spaced parallel relationship and said second guide includes a first plate and a second plate, positioned in a spaced parallel relationship.

2. The apparatus of claim 1, further comprising a system for providing a shielding gas to minimize oxidation and degradation of the plurality of curved suture needles as the plurality of suture needles pass through said housing.

3. The apparatus of claim 2, wherein the shielding gas is hydrogen, argon, nitrogen, neon, helium, CO, $CO_2$ or mixtures thereof.

4. The apparatus of claim 3, wherein said system for providing a shielding gas substantially prevents excessive heat transfer to the conveyer.

5. The apparatus of claim 1, wherein said conveyer comprises a strip or plurality of strips to which the plurality of curved suture needles are attached.

6. The apparatus of claim 5, wherein the plurality of curved suture needles are adhesively attached to the strip or plurality of strips.

7. The apparatus of claim 5, wherein the plurality of curved suture needles are welded to the strip or plurality of strips.

8. The apparatus of claim 5, wherein the source of curved suture needles comprises a pay-off spool.

9. The apparatus of claim 5, wherein the receiver comprises a take-up spool.

* * * * *